United States Patent
Riley et al.

(10) Patent No.: US 7,655,824 B2
(45) Date of Patent: Feb. 2, 2010

(54) PROCESSES FOR PRODUCING ALKYLBENZENES OVER SOLID ACID CATALYST AT LOW BENZENE TO OLEFIN RATIOS AND LOW HEAVIES MAKE

(75) Inventors: Mark G. Riley, Hinsdale, IL (US); Deng-Yang Jan, Elk Grove Village, IL (US); Stephen W. Sohn, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 133 days.

(21) Appl. No.: 11/872,783

(22) Filed: Oct. 16, 2007

(65) Prior Publication Data

US 2008/0161621 A1 Jul. 3, 2008

Related U.S. Application Data

(60) Provisional application No. 60/863,435, filed on Oct. 30, 2006.

(51) Int. Cl.
*C07C 2/58* (2006.01)
(52) U.S. Cl. ...................... 585/455; 585/467
(58) Field of Classification Search ............... 585/455, 585/467
See application file for complete search history.

(56) References Cited

U.S. PATENT DOCUMENTS

| | | | | |
|---|---|---|---|---|
| 3,641,177 | A | 2/1972 | Eberly et al. | 260/671 C |
| 4,310,440 | A | 1/1982 | Wilson et al. | 252/435 |
| 4,440,871 | A | 4/1984 | Lok et al. | 502/214 |
| 4,570,027 | A | 2/1986 | Boucher et al. | 585/455 |
| 4,731,497 | A * | 3/1988 | Grey | 585/455 |
| 4,793,984 | A | 12/1988 | Lok et al. | 423/306 |
| 4,876,408 | A | 10/1989 | Ratcliffe et al. | 585/467 |
| 4,990,718 | A * | 2/1991 | Pelrine | 585/455 |
| 5,196,574 | A | 3/1993 | Kocal | 562/94 |
| 5,434,326 | A | 7/1995 | Gajda et al. | 585/467 |
| 6,187,981 | B1 | 2/2001 | Marinangeli et al. | 585/323 |
| 6,315,964 | B1 | 11/2001 | Knifton et al. | 422/190 |
| 6,589,927 | B1 | 7/2003 | Kott et al. | 510/357 |
| 6,617,481 | B1 | 9/2003 | Kulprathipanja et al. | 585/323 |
| 6,670,516 | B1 | 12/2003 | Marinangeli et al. | 585/323 |
| 6,793,911 | B2 * | 9/2004 | Koegler et al. | 423/716 |
| 6,977,319 | B2 | 12/2005 | Campbell et al. | 585/455 |
| 2003/0147805 | A1 | 8/2003 | Koegler et al. | 423/700 |
| 2004/0097770 | A1 | 5/2004 | Dakka et al. | 585/467 |
| 2004/0162454 | A1 | 8/2004 | Gao et al. | 585/722 |
| 2005/0010072 | A1 | 1/2005 | Joly et al. | 585/449 |
| 2006/0142624 | A1 | 6/2006 | Harris et al. | 585/24 |
| 2008/0161617 | A1 | 7/2008 | Riley | |
| 2008/0161619 | A1 | 7/2008 | Riley et al. | |

OTHER PUBLICATIONS

Pujado, P.R.; "Linear Alkylbenzene (LAB) Manufacture" Handbook of Petroleum Refining Processes, edited by Robert A. Meyers, 2$^{nd}$ Edition, McGraw-Hill, New York, NY, USA (1996), pp. 1.53-1.66.
Gong et al., "Catalytic Performance of Nanometer MCM-49 Zeolite for Alkylation Reaction of Benzene with 1-Dodecene" Chinese Journal of Catalysis, vol. 25, No. 10, pp. 809-813, Oct. 2004.

\* cited by examiner

*Primary Examiner*—Thuan Dinh Dang
(74) *Attorney, Agent, or Firm*—Arthur E Gooding

(57) ABSTRACT

The alkylation of aromatic compound with acyclic mono-olefin is effected at low aromatic compound to mono-olefin ratios with reduced co-production of heavies. In the processes a small crystal, acidic FAU molecular sieve is used as a catalyst under alkylation conditions. This invention also relates to catalysts containing small crystal, acidic FAU molecular sieve and at least one other acidic catalytic component.

6 Claims, No Drawings

PROCESSES FOR PRODUCING ALKYLBENZENES OVER SOLID ACID CATALYST AT LOW BENZENE TO OLEFIN RATIOS AND LOW HEAVIES MAKE

CROSS-REFERENCE TO RELATED APPLICATIONS

This application claims priority from U.S. Provisional Patent Application No. 60/863,435, filed Oct. 30, 2006, which is incorporated by reference.

FIELD OF THE INVENTION

This invention pertains to processes for alkylating benzene with acyclic mono-olefin at low benzene to olefin ratios to provide alkylbenzenes having low heavies make by using solid, high activity catalysts containing small crystallite FAU molecular sieve. This invention also relates to catalysts containing small crystal, acidic FAU and at least one other acidic catalytic component.

BACKGROUND OF THE INVENTION

The alkylation of benzene with olefins is a widely practiced process, especially for the production of alkylbenzenes. Alkylbenzenes having alkyl groups of 8 to 14 carbon atoms per alkyl group, for instance, are commonly sulfonated to make surfactants. The alkylation conditions comprise the presence of homogeneous or heterogeneous alkylation catalyst such as aluminum chloride, hydrogen fluoride, or zeolitic catalysts and elevated temperature.

The catalysts are not selective and other reactions of olefins can occur to produce heavies, i.e., dimers, dialkylaryl compounds and diaryl compounds. Also, skeletal isomerization of the olefin can occur, resulting in a loss of selectivity to the sought alkylbenzene. The formation of dialkylaryl compounds is particularly problematic as the reaction approaches complete conversion of the olefin and the concentration of the alkylbenzene has thus increased thereby increasing the likelihood that an olefin molecule will react with an alkylbenzene molecule rather than benzene. Accordingly, typical processes use a large excess of benzene to reduce the molar ratio of the sought alkylbenzene to the olefin in the reactor. For homogeneous hydrogen fluoride catalyzed processes, the benzene to olefin ratio is generally in the range of 6:1 to 8:1. Solid catalysts are prone to generate more heavies. Hence, for these solid catalysts the mole ratio of benzene to olefin is typically greater than 15:1, often in excess of 20:1 and sometimes as much as 30:1.

The refining system for alkylbenzene production is summarized in Peter R. Pujado, Linear Alkylbenzene (LAB) Manufacture, Handbook of Petroleum Refining Processes, edited by Robert A. Meyers, Second Edition, McGraw-Hill, New York, N.Y., USA, (1996), pp 1.53 to 1.66, especially pages 1.56 to 1.60. Especially for large-scale, commercial alkylation processes such as are used for the production of linear alkylbenzenes, capital and operating costs can be very important, and the reboiler heat required to recover benzene from the alkylbenzene is a significant portion of the energy required in the refining system. Thus, as the ratio of benzene to olefin increases, material additional process costs are also incurred in the recovery and recycling of the unreacted benzene in the alkylation product.

Although the use of hydrogen fluoride as the alkylation catalyst is being used in commercial processes at lower benzene to olefin ratios, the use and handling of hydrogen fluoride does provide operational concerns due to its toxicity, corrosiveness and waste disposal needs. Solid catalytic processes have been developed that obviate the need to use hydrogen fluoride. However, the high benzene to olefin ratios required to minimize heavies make with these solid catalysts have rendered them unattractive to retrofit a production unit using hydrogen fluoride catalyst. Moreover, reducing the benzene to olefin ratio without increasing the amount of heavies produced would render solid acid catalyst processes more attractive for new facilities as compared to the hydrogen fluoride processes. Accordingly, solid catalytic processes are sought to further enhance their attractiveness through reducing energy costs and improving selectivity of conversion while still providing an alkylbenzene of a quality acceptable for downstream use such as sulfonation to make surfactants.

U.S. Pat. No. 3,641,177 discloses the use of steam stabilized hydrogen Y and rare earth-hydrogen Y zeolites containing less than 1% Na for catalyzing the alkylation of benzene with olefins.

U.S. Pat. No. 4,876,408 discloses the use of and ammonium exchanged, steam stabilized zeolite Y for selective monoalkylation of aromatics with olefins, especially ethylene and propylene.

U.S. Pat. No. 4,570,027 discloses the use of low crystallinity, partially collapsed zeolite for producing alkyl aromatic hydrocarbons. The preferred zeolite is zeolite Y. The patentees state that the process has a high degree of selectivity to the monoalkylated product.

U.S. Pat. No. 6,977,319B2 discloses processes for making alkylated aromatics using catalyst compositions comprising zeolite Y and mordenite zeolite having a controlled macropore structure.

US Application Publication 2003/0147805A1 discloses processes for making nanocrystalline inorganic based zeolite such as zeolite Y. The zeolite Y is stated to be useful in a number of hydrocarbon conversion processes including the preparation of linear alkylbenzenes.

US Application Publication 2004/0162454A1 discloses hydrocarbon conversion processes using nanocrystalline zeolite Y.

US Application Publication 2005/0010072A1 discloses an alkylation process using at least two catalysts in at least two distinct reaction zones. A preferred process uses Y zeolite in one reaction zone and mordenite in the other zone.

US Application Publication 2006/0142624A1 discloses zeolite Y catalysts having controlled macropore structures for alkylation.

Gong, et al., in Catalytic Performance of Nanometer MCM-49 Zeolite for Alkylation Reaction of Benzene with 1-Dodecene, Chinese Journal of Catalysis, Vol. 25, No. 10, 809-813, October 2004, relate increased activity with high selectivity for 2- and 3-phenylalkanes using MCM-49 having a diameter of 300 to 500 nanometers and a thickness of 20 to 25 nanometers.

SUMMARY OF THE INVENTION

By this invention processes are provided for the alkylation of aromatic compound with acyclic mono-olefin, especially benzene with olefin of 8 to 16 carbons per molecule, to produce phenylalkanes, which processes provide a product having desirable 2-phenyl content. In the preferred aspects of this invention, a low aromatic to mono-olefin mole ratio can be used without undue production of heavies, thereby enhancing the economic attractiveness of a solid catalyst alkylation process. The processes of this invention use alkylation catalyst comprising a catalytically effective amount of small crystal, acidic FAU molecular sieve.

In its broad aspect, the processes for producing alkylaromatic compound comprising contacting at least one aromatic compound and at least one acyclic mono-olefin in a molar ratio of aromatic compound to mono-olefin of less than about 15:1, preferably between about 4:1 to 12:1, and most preferably between about 5:1 to 10:1, with solid catalyst under alkylation conditions comprising the presence of catalyst containing small crystal, acidic FAU molecular sieve to provide an alkylation product comprising alkylaromatic compound wherein the Mono-alkylated Alkylaromatic Selectivity is at least about 92, preferably at least about 93, mass percent. Small crystal FAU molecular sieve has a major crystal dimension of less than about 500, preferably less than about 300, say, from about 50 to 300, nanometers. Preferably the alkylation conditions do not result in appreciable skeletal isomerization.

The term "Mono-alkylated Alkylaromatic Selectivity" is the mass percent of mono-alkylated alkylaromatic compound to total di- and polyalkylated alkylaromatic compound, diarylalkyl compound and olefin dimer in the alkylation product (excluding lighter molecular weight compounds than mono-alkylated aromatic compound of the olefin) and thus relates to heavies make.

In another broad aspect, this invention pertains to catalysts comprising a catalytically effective amount of small crystal, acidic FAU molecular sieve having a major crystal dimension of less than about 500 nanometers and a catalytically effective amount of solid acid catalytic component other than FAU molecular sieve. Preferably the solid acid catalytic component comprises at least one molecular sieve. The catalysts of this invention are particularly useful for the alkylation of aromatic compound with acyclic mono-olefin of 6 to 40, most frequently, 8 to 16, carbon atoms per molecule. For such uses, often the ratio of FAU molecular sieve to solid acid catalytic component is selected to provide a sought 2-phenyl content in the alkylated product.

DETAILED DISCUSSION OF THE INVENTION

The Feed and Products

Olefin-containing aliphatic compound and aromatic compound are used for the alkylation process. The selection of the olefin and aromatic compounds is dependent upon the sought alkylation product.

The olefin-containing aliphatic compound is preferably of about 6 to 40, often 8 to 28, and for detergent applications, 9 to 16, carbon atoms per molecule. The olefin-containing aliphatic compound is an acyclic, mono-olefinic compound. The positioning of the olefinic bond in the molecule is not critical as most alkylation catalysts have been found to promote migration of the olefinic bond. However, the branching of the hydrocarbon backbone is often more of a concern as the structural configuration of the alkyl group on the arylalkane product can affect performance especially in surfactant applications and for biodegradation properties. For instance, where arylalkanes are sulfonated to produce surfactants, undue branching can adversely affect the biodegradability of the surfactant. On the other hand, some branching may be desired such as the lightly branched modified alkylbenzenes such as described in U.S. Pat. No. 6,187,981B1. The olefin may be unbranched or lightly branched, which as used herein, refers to an olefin having three or four primary carbon atoms and for which none of the remaining carbon atoms are quaternary carbon atoms. A primary carbon atom is a carbon atom which, although perhaps bonded also to other atoms besides carbon, is bonded to only one carbon atom. A quaternary carbon atom is a carbon atom that is bonded to four other carbon atoms. Although branched, these alkylbenzenes have been characterized by their 2-phenyl content, see for instance, U.S. Pat. No. 6,589,927B1.

The olefin-containing aliphatic compound is usually a mixture of two or more olefins. For commercial processes, the feedstocks may include other components as well. These other components may comprise paraffins of about 6 to 40, often 8 to 28, and for detergent applications, 9 to 16, carbon atoms per molecule. For instance, the olefin may be obtained by the dehydrogenation of a paraffinic feedstock. See, for instance, U.S. Pat. No. 6,670,516B1, herein incorporated by reference. Generally, for the olefin-containing feedstock, the feedstock comprises at least about 10 mole percent olefin.

The source of the paraffinic feedstock is not critical although certain sources of paraffinic feedstocks will likely result in the impurities being present. Conventionally, kerosene fractions produced in petroleum refineries either by crude oil fractionation or by conversion processes therefore form suitable feed mixture precursors. Fractions recovered from crude oil by fractionation will typically require hydrotreating for removal of sulfur and/or nitrogen prior to being fed to the subject process. The boiling point range of the kerosene fraction can be adjusted by prefractionation to adjust the carbon number range of the paraffins. In an extreme case the boiling point range can be limited such that only paraffins of a single carbon number predominate. Kerosene fractions contain a very large number of different hydrocarbons and the feed mixture to the subject process can therefore contain 200 or more different compounds. The paraffinic feedstock may be at least in part derived from oligomerization or alkylation reactions. Such feed mixture preparation methods are inherently imprecise and produce a mixture of compounds. The feed mixtures to the process may contain quantities of paraffins having multiple branches and paraffins having multiple carbon atoms in the branches, cycloparaffins, branched cycloparaffins, or other compounds having boiling points relatively close to the desired compound isomer. The feed mixtures to the process of this invention can also contain aromatic hydrocarbons.

Another source of paraffins is in condensate from gas wells. Usually insufficient quantities of such condensate are available to be the exclusive source of paraffinic feedstock. However, its use to supplement other paraffinic feedstocks can be desirable. Typically these condensates contain sulfur compounds, which have restricted their use in the past. As this invention enables the use of sulfur-containing feeds, these condensates can be used to supply paraffins for alkylation.

Paraffins may also be produced from synthesis gas (Syngas), hydrogen and carbon monoxide. This process is generally referred to as the Fischer-Tropsch process. Syngas may be made from various raw materials including natural gas and coal, thus making it an attractive source of paraffinic feedstock where petroleum distillates are not available. The Fischer-Tropsch process is a catalytic process conducted under elevated temperature and pressure. The reaction is temperature sensitive, and temperature control is essential to achieve a desired hydrocarbon product. The products from the Fischer-Tropsch process include not only paraffins but also monoolefins, diolefins, aromatics and oxygenates such as alcohols, ethers, aldehydes and ketones, and thus are normally treated to eliminate oxygenates.

The olefin-containing feedstock should be sufficiently free of impurities that can unduly adversely affect the life of the alkylation catalyst.

The aromatic-containing feedstock to the subject process comprises an aromatic or a phenyl compound, which is benzene when the process is detergent alkylation. In a more general case, the aromatic or phenyl compound of the aromatic feedstock may be alkylated or otherwise substituted derivatives or of a higher molecular weight than benzene, including toluene, ethylbenzene, xylene, phenol, naphthalene, etc., but the product of such an alkylation may not be as suitable a detergent precursor as alkylated benzenes.

The Catalysts:

In accordance with the broad aspects of the processes of this invention the aromatic compound and mono-olefin is contacted with a catalyst comprising small crystal, acidic FAU molecular sieve. The FAU molecular sieve has a major crystal dimension of less than about 500, preferably less than about 300, say, from about 50 to 300, nanometers. Crystal size is measured visually by scanning electron microscope (SEM). It should be understood that the crystal sizes may vary within a sample and thus a catalyst within the scope of this invention may contain some larger or smaller sized crystals. In general, less than about 5 mass percent of the FAU crystals in a catalyst will be greater than 500 nanometers in major dimension. The FAU and other zeolite framework types are described in Ch. Baerlocher, W. M. Meier and D. H. Olson, "Atlas of Zeolite Framework Types", 5$^{th}$ ed., Elsevier: Amsterdam, 2001, which is herein incorporated by reference.

Preferably the acidic FAU molecular sieve has an acidity of at least about 0.10, preferably at least about 0.12, and sometimes at least about 0.2, millimole of ammonia per gram of dry FAU molecular sieve as determined by ammonia temperature programmed desorption (ammonia TPD). The ammonia TPD process is performed at ambient pressure and involves first heating a sample (about 250 milligrams) of FAU molecular sieve at a rate of about 5° C. per minute to a temperature of about 550° C. in the presence of an 20 volume percent oxygen in helium atmosphere (flow rate of about 100 milliliters per minute). After a hold of about one hour, helium is used to flush the system (about 15 minutes) and the sample is cooled to about 150° C. The sample is then saturated with pulses of ammonia in helium at about 40 milliliters per minute. The total amount of ammonia used is greatly in excess of the amount required to saturate all the acid sites on the sample. The sample is purged with helium (about 40 milliliters per minute) for about 8 hours to remove physisorbed ammonia. With the helium purge continuing, the temperature is increased at a rate of about 10° C. per minute to a final temperature of 600° C. The amount of ammonia desorbed is monitored using a calibrated thermal conductivity detector. The total amount of ammonia is found by integration. Dividing the total amount of ammonia by the dry weight of the sample yields the acidity expressed as millimoles of ammonia per gram of dry sample. The dry weight of the molecular sieve can be determined by heating the molecular sieve in flowing nitrogen at 500° C. for 2 hours.

The preferred FAU molecular sieves include zeolite Y, dealuminated zeolite Y and zeolite X, including rare earth exchanged zeolites Y and X, having a framework silica to alumina molar ratio of between about 2:1 to 70:1, preferably about 5:1 to 30:1. The FAU molecular sieve is often in a hydrogen form.

The FAU molecular sieve may be synthesized in any convenient manner. See, for instance, U.S. Application Publication 2003/0147805A1 and U.S. Application Publication 2004/0162454A1, both herein incorporated by reference. The FAU molecular sieve may be treated in any suitable manner such as by steaming or acid treatment, although in the broad aspects of this invention, such treatment is not essential.

The catalyst may contain other molecular sieves or alkylation catalysts to provide a product of a sought 2-phenyl content. Where the alkylaromatic compound is an alkylbenzene, one of its primary uses is for making surfactants. Alkylbenzenes, to be desirable for making sulfonated surfactants must be capable of providing a sulfonated product of suitable clarity, biodegradability and efficacy. With respect to efficacy, alkylbenzenes having higher 2-phenyl contents are desired as they tend, when sulfonated, to provide surfactants having better solubility and detergency. Thus alkylbenzenes having a 2-phenyl isomer content in the range from about 18 to about 40 mass percent are particularly desired. FAU molecular sieve tends to provide an alkylbenzene having a 2-phenyl content of about 18 to 26 mass percent. Copending patent application, filed on even date herewith, discloses the use of UZM-8 molecular sieve as a co-catalyst with FAU molecular sieve to provide an alkylbenzene product having a 2-phenyl content of between about 25 and 40 mass percent (based upon total phenylalkane), preferably, between about 26 and 36 mass percent. The UZM-8 molecular sieve is described in U.S. Pat. No. 6,756,030B1, hereby incorporated in its entirety. Advantageously, with UZM-8, the 2-phenyl content remains relatively constant between catalyst regenerations and over the life of the catalyst. Moreover, UZM-8 typically provides a low heavies make. Other catalytic components that may find application in providing a catalyst with small crystal zeolite Y include one or more of the following molecular sieves: ZSM-4, ZSM-12, ZSM-20, ZSM-38, MCM-22, MCM-36, MCM-49, beta, molecular sieves of the MOR zeolite framework type, molecular sieves of the OFF zeolite framework type, and molecular sieves of the LTL zeolite framework type. These molecular sieves preferably have one crystal dimension that has a maximum size of less than about 500, preferably less than about 300, say, from about 50 to 300, nanometers. Another class of acidic, solid catalyst components are acidified refractory oxides such as chlorided, fluorided, or sulfated alumina, gallia, boria, molybdia, ytterbia, titania, chromia, silica, zirconia, and the like and combinations thereof. Clays and amorphous catalysts may also find utility. Further discussion of alkylation catalysts can be found in U.S. Pat. Nos. 5,196,574; 6,315,964B1 and 6,617,481B1. The amount of the additional molecular sieve is generally selected to provide the sought 2-phenyl content.

The catalyst contains a catalytically-effective amount of molecular sieve. The catalyst may contain suitable binder or matrix material such as inorganic oxides and other suitable materials. The relative proportion of molecular sieve in the catalyst may range from about 10 to about 99 mass-percent, with about 20 to about 90 mass-percent being preferred.

A refractory binder or matrix is typically used to facilitate fabrication of the catalyst, provide strength and reduce fabrication costs. The binder should be uniform in composition and relatively refractory to the conditions used in the process. Suitable binders include inorganic oxides such as one or more of alumina, magnesia, zirconia, chromia, titania, boria and silica. The catalyst also may contain, without so limiting the composite, one or more of (1) other inorganic oxides including, but not limited to, beryllia, germania, vanadia, tin oxide, zinc oxide, iron oxide and cobalt oxide; (2) non-zeolitic molecular sieves, such as the aluminophosphates of U.S. Pat. No. 4,310,440, the silicoaluminophosphates of U.S. Pat. No. 4,440,871 and ELAPSOs of U.S. Pat. No. 4,793,984; and (3) spinels such as MgAl2O4, FeAl2O4, ZnAl2O4, CaAl2O4, and other like compounds having the formula MO—Al2O3 where M is a metal having a valence of 2; which components can be added to the composite at any suitable point.

The catalyst may be prepared in any suitable manner. One method for preparation involves combining the binder and molecular sieve in a hydrosol and then gelling the mixture. One method of gelling involves combining a gelling agent with the mixture and then dispersing the resultant combined mixture into an oil bath or tower which has been heated to elevated temperatures such that gellation occurs with the formation of spheroidal particles. The gelling agents which may be used in this process are hexamethylene tetraamine, urea or mixtures thereof. The gelling agents release ammonia at the elevated temperatures which sets or converts the hydrosol spheres into hydrogel spheres. The spheres are then continuously withdrawn from the oil bath and typically subjected to specific aging and drying treatments in oil and in ammoniacal solution to further improve their physical characteristics. The resulting aged and gelled particles are then washed and dried at a relatively low temperature of about 100° to 150° C. and subjected to a calcination procedure at a temperature of about 450° to 700° C. for a period of about 1 to 20 hours.

The combined mixture preferably is dispersed into the oil bath in the form of droplets from a nozzle, orifice or rotating disk. Alternatively, the particles may be formed by spray-drying of the mixture at a temperature of from about 425° to 760° C. In any event, conditions and equipment should be selected to obtain small spherical particles; the particles preferably should have an average diameter of less than about 5.0 mm, more preferably from about 0.2 to 3 mm, and optimally from about 0.3 to 2 mm.

Alternatively, the catalyst may be an extrudate. A multitude of different extrudate shapes are possible, including, but not limited to, cylinders, cloverleaf, dumbbell and symmetrical and asymmetrical polylobates. Typical diameters of extrudates are 1.6 mm (1/16 in.) and 3.2 mm (1/8 in.). The extrudates may be further shaped to any desired form, such as spheres, by any means known to the art.

The catalyst of the present invention may contain a halogen component, e.g., about 0.1 to about 4 mass percent halogen. A suitable halogen is, for example, fluoride. Frequently the catalyst need not contain any added halogen other than that associated with other catalyst components to provide the sought alkylation activity.

The catalytic composite optimally is subjected to steaming to tailor its acid activity. The steaming may be effected at any stage of the zeolite treatment. Alternatively or in addition to the steaming, the composite may be washed with one or more of a solution of ammonium nitrate; a mineral acid such as hydrogen chloride, sulfuric acid or nitric acid; and/or water.

If desired, the catalytic composite usually is dried and then calcined, e.g., at a temperature of from about 400° C. to about 600° C. in an air atmosphere for a period of from about 0.1 to 10 hours.

The Processes:

The acyclic mono-olefin is reacted with aromatic compound to produce arylalkane, or phenylalkane. Preferably, the aromatic compound is alkylated with a single mono-olefin.

With respect to the overall alkylation process, usually the aromatic compound is present in a stoichiometric excess to the mono-olefin, e.g., from about 2.5:1 up to about 15:1 and normally from about 4:1 to about 12:1, on a molar basis. The processes of this invention are particularly attractive in that low heavies make can be achieved even at lower aromatic compound to olefin mole ratios. In the preferred aspects of the processes of this invention, the aromatic compound to olefin mole ratio is between about 5:1 to 10:1 or about 5:1 to 8:1. The heavies, even at these low ratios, may often be less than about 6 mass percent of the phenylalkane product.

The aromatic or phenyl compound and the olefin are reacted under alkylation conditions in the presence of the catalyst. These alkylation conditions for both catalysts generally include a temperature in the range between about 80° C. and about 200° C., most usually at a temperature not exceeding about 175° C. Where different reaction zones are used, each reaction zone may be at different alkylation conditions within these ranges or, preferably, the reaction zones are under common temperature and pressure conditions for ease of operation. The benefits of this invention can still be achieved using common temperature and pressure conditions. Similarly, the reaction zones may provide the same or different space velocities.

Since the alkylation is typically conducted in at least partial liquid phase, and preferably in either an all-liquid phase or at supercritical conditions, pressures must be sufficient to maintain reactants in the liquid phase. The requisite pressure necessarily depends upon the olefin, the aryl compound, and temperature, but normally is in the range of about 1300 to 7000 kPa(g), and most usually between about 2000 and 3500 kPa(g). Preferably the alkylation conditions do not substantially result in skeletal isomerization of the olefin. For instance, less than 15 mole percent, and preferably less than 10 mole percent, of the olefin, the aliphatic alkyl chain, and any reaction intermediate undergoes skeletal isomerization.

Alkylation of the aromatic compound by the olefins is conducted in a continuous manner. For purposes herein, a catalyst bed is termed a reaction zone whether in the same or a separate vessel from another bed. The number of reaction zones is preferably at least two, and is often three or more. In the processes of this invention 3 or 4 reaction zones can be used for an advantageous combination of performance and capital expense avoidance. Co-pending patent application, filed on even date herewith discloses a multiple bed alkylation reactor system with interbed cooling to provide an alkylbenzene product having enhanced linearity.

The catalyst may be used as a packed bed or a fluidized bed. The feed to the reaction zone may be passed either upflow or downflow, or even horizontally as in a radial bed reactor. In one desirable variant, olefin-containing feedstock may be fed into several discrete points within the reaction zone, and at each zone the aromatic compound to olefin molar ratio may be greater than 50:1. The total feed mixture, that is, aromatic compound plus the olefin-containing stream, is often passed through the packed bed at a liquid hourly space velocity (LHSV) between about 0.3 and about 6 hr-1 depending upon, e.g., alkylation temperature and the activity of the catalyst. Where more than one catalyst bed is used in series, the overall LHSV is determined from the LHSV's of each of the beds. The reciprocal of the overall LHSV is the sum of the reciprocals of the LHSV of each of the beds in series.

After passage of the aromatic compound and the olefin through the reaction zone, the effluent is collected and separated into unreacted aromatic compound fraction, which is recycled to the feed end of the reaction zone, and arylalkanes. Where the olefin is obtained by the dehydrogenation of a paraffinic feedstock, any paraffins in the reaction zone effluent are usually separated into a paraffinic fraction, which may be recycled to the dehydrogenation unit. Since the reaction usually goes to at least about 98% conversion based on the olefin, little unreacted olefin is recycled with paraffin.

EXAMPLES

Example 1 (Comparative)

Catalyst A is composed of 80% Y zeolite that has been ammonium exchanged, steamed dealuminated, ammonium exchanged, steamed dealuminated and then acid extracted to remove extra framework alumina. These techniques are well known and Y zeolites produced using these techniques are commercially available from a number of companies. The Y zeolite has a silicon to aluminum molar ratio of around 7, a unit cell size (UCS) of 24.29 angstroms and a crystal size of approximately 1.5 microns. The zeolite is bound with alumina and extruded into 1.6 mm (1/16 in.) diameter cylinders using ordinary techniques and then calcined at 600° C.

Catalyst A is evaluated in a plug flow reactor at a molar ratio of benzene to olefin of 30:1 under the following conditions: inlet temperature of 130° C. and LHSV of 3.75 hr$^{-1}$.

The olefins are sourced from a commercial plant. The olefin-containing stream contains approximately 12 mass % olefins with the remainder consisting of mostly n-paraffins.

The products of the alkylation are analyzed by gas chromatography (GC) to determine product distribution and by bromine index to determine the amount of unreacted olefin. The olefin conversion is greater than 99.5% and the product distribution is given in Table 1. The heavier molecular weight alkylation products are substantially dialkylbenzene and thus the heavies are reported in Table 1 as dialkylbenzene.

TABLE 1

| | |
|---|---|
| Linear monoalkylbenzene | 89%-mass |
| Non-linear monoalkylbenzene | 8%-mass |
| Total monoalkylate | 97%-mass |
| Dialkylbenzene | 3%-mass |
| 2-phenyl LAB/total monoalkylbenzene | 22%-mass |

Catalyst A is evaluated in a plug flow reactor at a molar ratio of benzene to olefin of 10:1 at an inlet temperature of 130° C., and at a LHSV of 2.2 hr$^{-1}$. using a similar feedstock:

The olefin conversion is greater than 99.5% and the product distribution is given in Table 2:

TABLE 2

| | |
|---|---|
| Linear monoalkylbenzene | 84%-mass |
| Non-linear monoalkylbenzene | 8%-mass |
| Total monoalkylate | 92%-mass |
| Dialkylbenzene | 8%-mass |
| 2-phenyl LAB/total monoalkylbenzene | 21%-mass |

As can be seen from the above, a reduction in the benzene to olefin ratio results in a more than doubling of the make of dialkylbenzenes.

Example 2

Catalyst B is composed of 80% zeolite Y having a silicon to aluminum molar ratio of between about 7:1 and a crystal size of about 300 nanometers in major dimension. The zeolite Y is bound with alumina and extruded into 1.6 mm (1/16 in.) diameter cylinders using ordinary techniques and then calcined at 600° C.

Catalyst B is evaluated for alkylation performance using a similar feedstock to that used in Example 1. The olefin conversion is greater than 99.5% and the product distributions are given in Tables 3-5.

The product distribution at a benzene to olefin molar ratio of 30:1 (comparative), inlet temperature of 90° C., and 3.79 hr–1 LHSV is in Table 3:

TABLE 3

| | |
|---|---|
| Linear monoalkylbenzene | 90.4%-mass |
| Non-linear monoalkylbenzene | 6.6%-mass |
| Total monoalkylate | 97.0%-mass |
| Dialkylbenzene | 2.2%-mass |
| Lights | 0.9%-mass |
| Mono-alkylated Alkylaromatic Selectivity | 97.9%-mass |
| 2-phenyl LAB/total monoalkylbenzene | 21.4%-mass |

The product distribution at a benzene to olefin molar ratio of 10:1, inlet temperature of 110° C., and 2.22 hr$^{-1}$ LHSV is in Table 4:

TABLE 4

| | |
|---|---|
| Linear monoalkylbenzene | 84.6%-mass |
| Non-linear monoalkylbenzene | 9.3%-mass |
| Total monoalkylate | 93.9%-mass |
| Dialkylbenzene | 4.8%-mass |
| Lights | 1.3%-mass |
| Mono-alkylated Alkylaromatic Selectivity | 95.1%-mass |
| 2-phenyl LAB/total monoalkylbenzene | 21.2%-mass |

The product distribution at a benzene to olefin molar ratio of 6:1, inlet temperature of 115° C., and 1.97 hr$^{-1}$ LHSV is in Table 5:

TABLE 5

| | |
|---|---|
| Linear monoalkylbenzene | 81.7%-mass |
| Non-linear monoalkylbenzene | 10.3%-mass |
| Total monoalkylate | 92.0%-mass |
| Dialkylbenzene | 6.7%-mass |
| Lights | 1.3%-mass |
| Mono-alkylated Alkylaromatic Selectivity | 93.2%-mass |
| 2-phenyl LAB/total monoalkylbenzene | 21.1%-mass |

Surprisingly, at a 30:1 benzene to olefin molar ratio, the benefit provided by using small crystal Y molecular sieve is less than that at lower benzene to olefin ratios, as shown in Table 6:

TABLE 6

| Benzene:Olefin, mole/mole | Ex. 1 Y Dialkylbenzene, %-mass | Ex. 2 Y Dialkylbenzene, %-mass | Reduction, Mass % |
|---|---|---|---|
| 30:1 | 3 | 2.2 | 27 |
| 10:1 | 8 | 4.8 | 40 |

It is claimed:

1. A process for producing alkylaromatic compound comprising contacting at least one aromatic compound and at least one acyclic mono-olefin of 6 to 40 carbon atoms per molecule in a molar ratio of aromatic compound to mono-olefin between about 5:1 to about 10:1 with solid catalyst under alkylation conditions comprising the presence of catalyst containing small crystal, acidic Y zeolite to provide an alkylation product comprising alkylaromatic compound wherein the Mono-alkylated Alkylaromatic Selectivity is at least about 92, wherein the Y zeolite has a major crystal dimension of from about 50 to about 300 nanometers and where the amount of dialkylbenzene in the alkylation product is reduced by at least 40 mass-% as compared to when the Y zeolite has a major crystal dimension of about 1.5 microns.

2. The process of claim 1 wherein the Mono-alkylated Alkylaromatic Selectivity of the alkylation product is at least about 93 mass percent.

3. A process for producing alkylaromatic compound comprising contacting at least one aromatic compound and at least one acyclic mono-olefin of 6 to 40 carbon atoms per molecule in a molar ratio of aromatic compound to mono-olefin between about 5:1 to about 10:1 with solid catalyst under alkylation conditions comprising the presence of catalyst containing small crystal, acidic Y zeolite to provide an alkylation product comprising alkylaromatic compound and no more than about 4.8 mass-% dialkylbenzene, wherein the Mono-alkylated Alkylaromatic Selectivity is at least about 92, wherein the Y zeolite has a major crystal dimension of from about 50 to about 300 nanometers.

4. The process of claim 3 wherein the Mono-alkylated Alkylaromatic Selectivity of the alkylation product is at least about 93 mass percent.

5. A process for controlling the dialkylbenzene produced in an alkylaromatic producing process comprising: contacting at least one aromatic compound and at least one acyclic mono-olefin of 6 to 40 carbon atoms per molecule in a molar ratio of aromatic compound to mono-olefin between about 5:1 to about 10:1 with solid catalyst under alkylation conditions comprising the presence of catalyst containing small crystal, acidic Y zeolite to provide an alkylation product comprising alkylaromatic compound and no more than about 4.8 mass-% dialkylbenzene, wherein the Mono-alkylated Alkylaromatic Selectivity is at least about 92, wherein the Y zeolite has a major crystal dimension of from about 50 to about 300 nanometers.

6. The process of claim 5 wherein the Mono-alkylated Alkylaromatic Selectivity of the alkylation product is at least about 93 mass percent.

* * * * *